US010729504B2

(12) United States Patent
Schaller (10) Patent No.: US 10,729,504 B2
(45) Date of Patent: Aug. 4, 2020

(54) SYSTEMS AND METHODS FOR A SURGICAL TISSUE MANIPULATOR

(71) Applicant: Novartis AG, Basel (CH)

(72) Inventor: Philipp Schaller, Stein am Rhein (CH)

(73) Assignee: Alcon Inc., Rue Louis-d'affry, Fribourg (CH)

( * ) Notice: Subject to any disclaimer, the term of this patent is extended or adjusted under 35 U.S.C. 154(b) by 234 days.

(21) Appl. No.: 15/831,941

(22) Filed: Dec. 5, 2017

(65) Prior Publication Data

US 2018/0092702 A1    Apr. 5, 2018

Related U.S. Application Data

(62) Division of application No. 14/090,305, filed on Nov. 26, 2013, now abandoned.

(51) Int. Cl.
*A61B 34/00* (2016.01)
*A61F 9/007* (2006.01)

(52) U.S. Cl.
CPC .......... *A61B 34/70* (2016.02); *A61F 9/00727* (2013.01)

(58) Field of Classification Search
CPC ....... A61B 17/221; A61B 17/29; A61B 17/30; A61B 17/3421; A61B 17/00234; A61B 17/0218; A61B 17/32056; A61B 17/0231; A61B 17/22031; A61B 17/320725; A61B 2090/306; A61B 2017/2215; A61B 2017/00867; A61B 2017/0464; A61B 2017/22034; A61B 1/313; A61B 34/70; A61B 3/12; A61F 9/00727; A61F 9/00736; A61F 9/007; A61F 9/0017; A61F 9/008

See application file for complete search history.

(56) References Cited

U.S. PATENT DOCUMENTS

| | | | | |
|---|---|---|---|---|
| 4,878,487 A | * | 11/1989 | Sinnett ................ | A61F 9/00727 600/236 |
| 2008/0027396 A1 | * | 1/2008 | Meyer .................. | A61F 9/0017 604/198 |
| 2008/0269774 A1 | * | 10/2008 | Garcia ................. | A61B 17/221 606/127 |
| 2009/0036900 A1 | * | 2/2009 | Moll .................... | A61G 7/0503 606/130 |

* cited by examiner

*Primary Examiner* — Elizabeth Houston
*Assistant Examiner* — Mohamed G Gabr (57) ABSTRACT

An apparatus for manipulating tissue during a procedure performed within an eye of a patient is disclosed herein. The apparatus includes a hand-held controller and an elongate member configured to be inserted into the eye of the patient. The elongate member has a proximal end and a distal end, with the proximal end of the elongate member being coupled to the hand-held controller. The elongate member also has a lumen extending through the length of the elongate member. The apparatus further includes a plurality of flexible grasping fibers extending through at least a portion of the lumen and beyond the distal end thereof. The grasping fibers are adjustable by the hand-held controller to advance or retract relative to the elongate member by altering a distance between distal ends of the grasping fibers and the distal end of the elongate member.

4 Claims, 9 Drawing Sheets

SYSTEMS AND METHODS FOR A SURGICAL TISSUE MANIPULATOR

PRIORITY

This application is a divisional application of U.S. patent application Ser. No. 14/090,305 titled "Systems and Methods for a Surgical Tissue Manipulator" which was filed Nov. 26, 2013 whose inventor is Philipp Schaller which is hereby incorporated by reference in its entirety as though fully and completely set forth herein.

BACKGROUND

The present disclosure relates to systems and methods as used to manipulate delicate tissue during surgical procedures, and more particularly, to the manipulation of retinal tissue during an ophthalmic surgical procedure.

Among the many conditions that can afflict a patient's eye are retinal detachment and/or tearing. A detached retina is a condition in which the retina of an eye, which is normally attached at the back of the eye, peels away from the back of the eye. This can cause vision problems including blindness. In order to reattach the retina, surgery may be required. During a procedure, the retina may be manipulated back into position against the back of the eye. However, retinal tissues are easily damaged during manipulation. Current approaches to manipulate and reposition a detached retina include grasping, squeezing, and manipulating the retina with internal limiting membrane (ILM) forceps. However, this approach may concentrate excessive pressure on the retinal tissues. Other approaches, such as the use of backflush soft tip instruments do not provide the ability to grasp tissue. Thus, the current approaches may cause additional damage to the detached retina during the reattachment process due to the high surface pressure of such forceps.

Therefore, there remains a need for an improved systems and methods for manipulating retinal tissue. The present disclosure is directed to addressing one or more of the deficiencies in the prior art.

SUMMARY

In one exemplary aspect, the present disclosure is directed to an apparatus for manipulating tissue during a procedure performed within an eye of a patient. The apparatus includes a hand-held controller and an elongate member configured to be inserted into the eye. The elongate member has a proximal end and a distal end, with the proximal end of the elongate member being coupled to the hand-held controller. The elongate member also has a lumen extending through the length of the elongate member. The apparatus further includes a plurality of flexible grasping fibers extending through at least a portion of the lumen and beyond the distal end thereof. The grasping fibers are adjustable by the controller to advance or retract relative to the elongate member by altering a distance between distal ends of the grasping fibers and the distal end of the elongate member.

In another exemplary aspect, the present disclosure is directed to an apparatus for manipulating tissue in an eye of a patient. The apparatus is inserted with minimal invasiveness into the patient and includes an elongate member configured to be inserted through a minimally invasive surgical opening in the eye of the patient. The elongate member has a proximal end, a distal end, and a lumen extending through the length of the elongate member. The apparatus further includes a hand-held controller coupled to the proximal end and a plurality of grasping fibers extending through at least a portion of the lumen and beyond the distal end thereof The plurality of grasping fibers is adjustable by the hand-held controller to grasp a portion of the tissue by altering a distance between distal ends of the grasping fibers and the distal end of the elongate member.

In another exemplary aspect, the present disclosure is directed to a method of positioning retinal tissue that has detached from a back surface of an eye of a patient. The method includes steps of making an incision in the eye and inserting a retinal manipulator into the eye through the incision. The retinal manipulator has two pluralities of grasping fibers at a distal end thereof. The method further includes grasping a portion of the retinal tissue that is detached from the back surface of the eye between the two pluralities of grasping fibers and of maneuvering the retinal tissue by maneuvering the grasped portion with the retinal manipulator.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

These figures are better understood by reference to the following Detailed Description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the present disclosure is intended. Any alterations and further modifications to the described devices, instruments, methods, and any further application of the principles of the present disclosure are fully contemplated as would normally occur to one skilled in the art to which the present disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods of manipulating delicate tissue such as retinal tissue, particularly when the tissue is accessed during a minimally invasive procedure. In some aspects, in order to handle the retinal tissue in a suitably gentle manner, the grasping pressure on the tissue is distributed across more than two or three surfaces. As disclosed herein, a plurality of fingers or fibers is controlled to provide such a distributed surface for safer grasping of the retina of a patient. While the example of retinal manipulation is used throughout this disclosure, the systems and methods may be applied for the manipulation of other delicate tissues.

Figure 1:
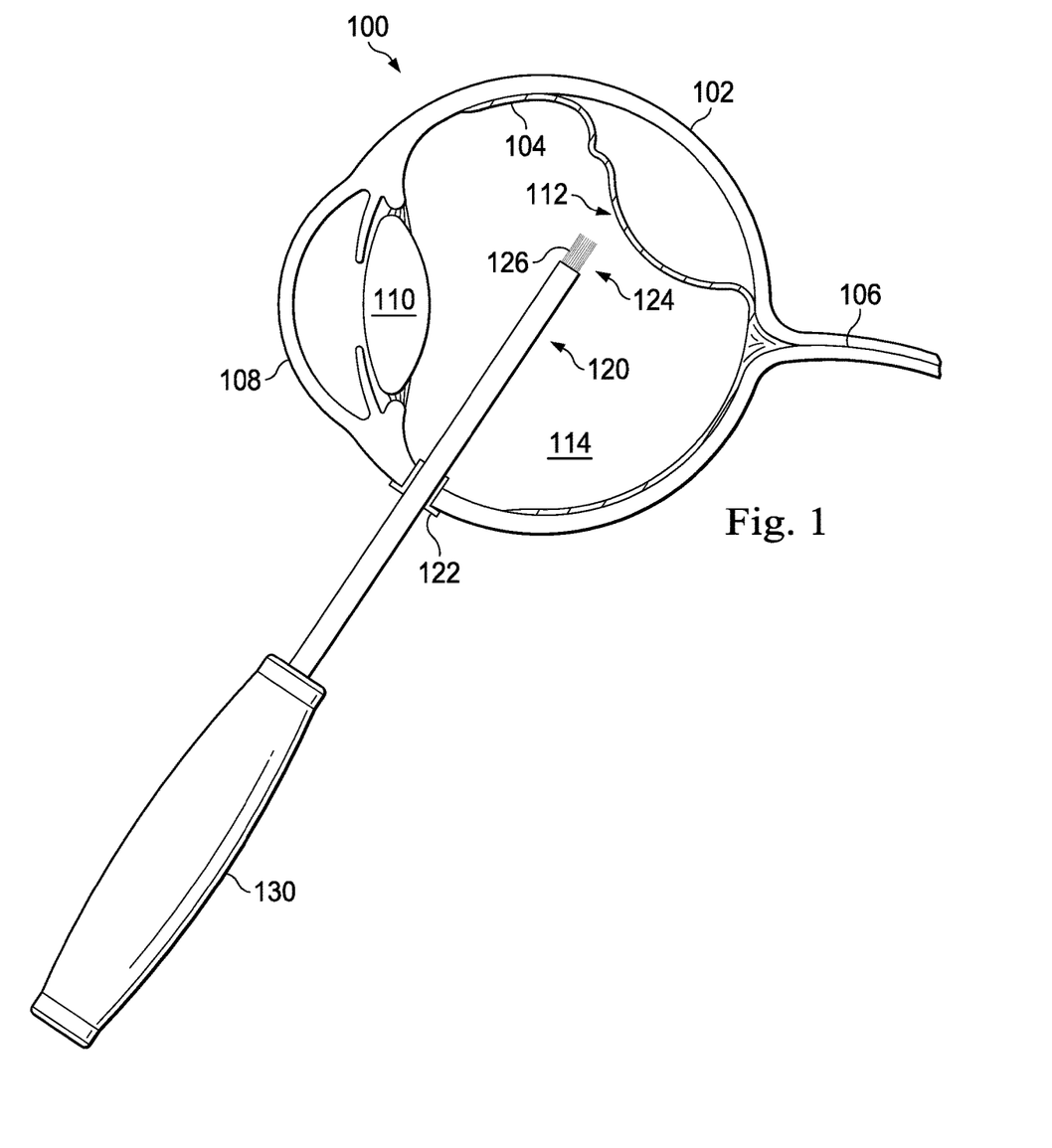
FIG. 1 is a cross-sectional illustration of a retinal manipulator, according to exemplary aspects of the present disclosure, inserted into an eye.

FIG. 1 is a cross-sectional illustration of an eye 100 having a retinal manipulator 120 inserted therein according to exemplary aspects of the present disclosure. A number of features of the eye 100 are illustrated herein. The eye 100 includes a sclera 102 that is coupled to a retinal membrane or retina 104 by a choroid (not illustrated in FIG. 1). The choroid includes connective tissue to attach the retina 104 to the inside wall of the sclera 102 at the back of the eye 100 and to provide oxygen and nourishment to the outer layers of the retina 104. The retina 102 contains photo-activated cells that transmit signals over an optic nerve 106 to a brain. A cornea 108 permits light to enter the eye 100, the light being focused by a lens 110.

As illustrated, the eye 100 includes a pronounced detachment area 112 in which the retina 104 is detached from the back, inner wall of the sclera 102. Fluid or vitreous humor may fill an area between the detached portion of the retina 104 and the sclera 102. To treat the detachment 112, the detached portion of the retina 104 may be repositioned against the sclera 104. As part of this process, a vitrectomy procedure may be performed to remove vitreous humor from the vitreous chamber 114 of the eye 100. After the retina 104 is properly positioned, it may be reattached naturally over a period of time.

Properly repositioning the retina 104 against the sclera 102 may be done by manually grasping the retina 104 and moving it into the desired position. The retinal manipulator 120 is an apparatus configured to distribute a grasping force over a larger surface area so that additional damage to the retina 104 may be avoided during the effort to reposition it. The retinal manipulator 120 is introduced into the vitreous chamber 114 through an opening in the sclera 102 provided by a trocar cannula 122. A distal portion 124 of the manipulator 120 includes a plurality of fingers or grasping fibers 126 that may be used to securely grasp the retina 104 for precise positioning. The plurality of grasping fibers 126 may provide a distributed contact area by which to grasp the retina 104. This may prevent damage that can be caused when small contact surfaces are used that cause high surface pressure that is difficult to control, such as may be the case with conventional forceps. A proximal end of the manipulator 120 includes a hand-held controller 130. The hand-held controller is configured to provide for manual or automatic control of the distal portion 124 of the retinal manipulator. Further detail regarding the manipulator 120 is included below.

Figure 2A:
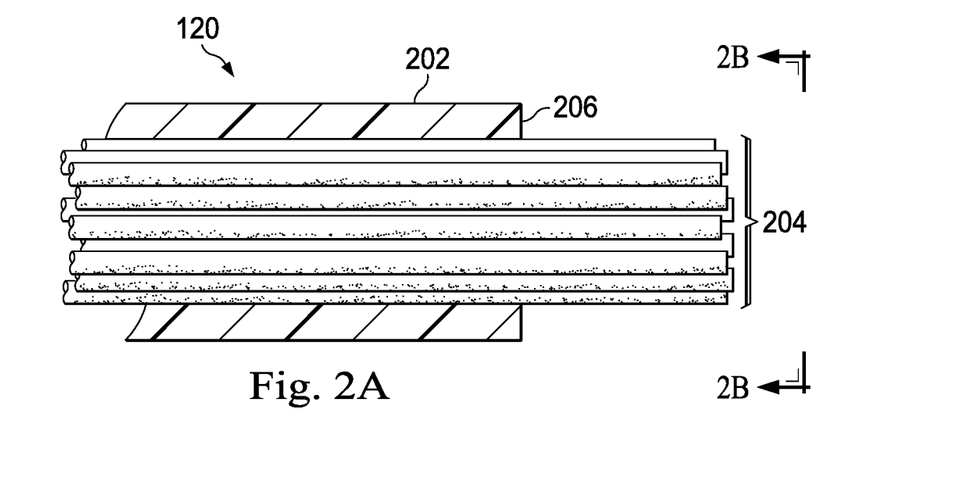
FIG. 2A is a cross-sectional illustration of a retinal manipulator in a closed state according to exemplary aspects of the present disclosure.

FIG. 2A is a cross-sectional illustration of a retinal manipulator 120 such as that described in FIG. 1. Only a distal portion of the manipulator 120 is depicted in FIG. 2A. The manipulator 120 includes an elongate member illustrated as a tube 202 that contains a plurality of grasping fibers 204 in a lumen extending at least part way through the tube 202. The tube 202 includes a distal end 206 and a proximal end (not depicted). The tube 202 and the grasping fibers 204 may not be fixed together. Rather, the tube 202 may slide away from or toward the exposed distal ends of the plurality of grasping fibers 204. The relative positioning of the distal end 206 of the tube 202 and the distal ends of the grasping fibers 204 may adjust the stiffness of the grasping fibers 204 and their position and orientation within the eye of a patient. FIG. 2A illustrates the manipulator 120 in a "closed" state. In some embodiments, the tube 202 may be about 1.5 inches in length.

Figure 2B:
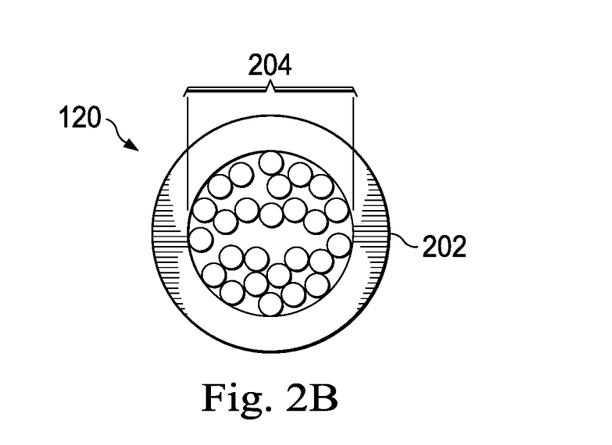
FIG. 2B is an end view of the retinal manipulator illustrated in FIG. 2A.

FIG. 2B is an end view of the retinal manipulator 120 illustrated in FIG. 2A. In the illustrated embodiment of FIG. 2B, the tube 202 has a generally circular cross-section and the grasping fibers 204 similarly have circular cross-sections. In some embodiments, other cross-sections may be used. For example, the tube 202 may have an elliptical cross-section.

Figure 2C:
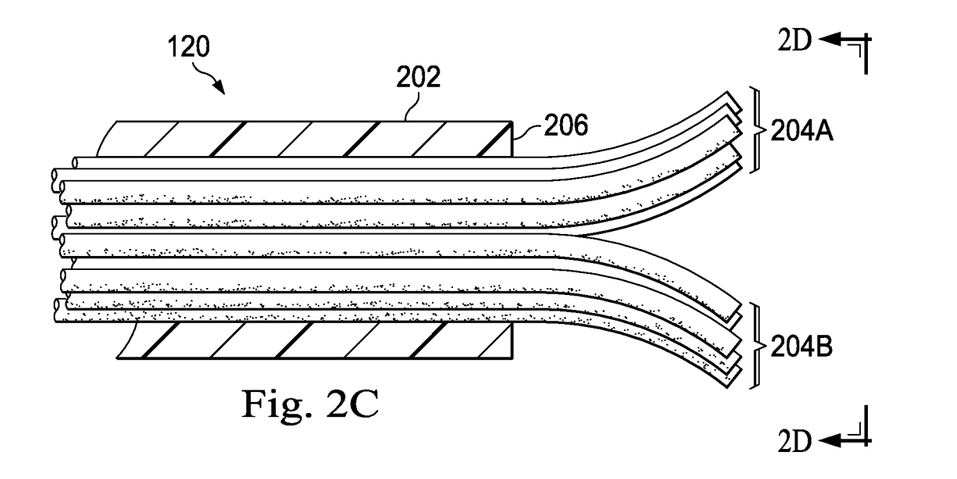
FIG. 2C is a cross-sectional illustration of the retinal manipulator of FIGS. 2A and 2B in an open state according to exemplary aspects of the present disclosure.

FIG. 2C is a cross-sectional illustration of the retinal manipulator of FIGS. 2A and 2B in an "open" state according to exemplary aspects of the present disclosure. Unlike in FIGS. 2A and 2B, the manipulator 120 as illustrated in FIG. 2B is in an open state, such that the distal ends of all the grasping fibers 204 are not compressed together. Each of the grasping fibers is formed with a desired curvature, such that when no force is applied to a grasping fiber, it exhibits a curved shape or is biased in a curved shape. That is, its natural shape absent deforming forces is a curved shape. However, when a force is applied to a grasping fiber, such as by drawing it into a confined volume, the limits of the volume may temporarily straighten the grasping fiber. The grasping fibers 204 are formed such that there is a curved portion at the distal ends of the fibers 204. When the curved portions at the distal ends of the grasping fibers 204 are draw into the tube 202, the fibers 204 are forced into a straight configuration. The curved portions of the grasping fibers 204 are resilient or elastic such that the tendency to curve is not eliminated by temporary positioning of the grasping fibers 204 within the confinement of the tube 202.

The grasping fibers 204 include two groups of fibers 204: an "up" group 204A and a "down" group 204B. As illustrated, the grasping fibers in the up group 204A are predisposed or preformed to curve upwards when in their natural shape, while the grasping fibers in the down group 204B are preformed to curve downwards when in their natural shape. Thus, the up group 204A and the down group 204B are configured to curve away from each other in opposing directions. In some aspects, this may be achieved by a difference in arrangement of the grasping fibers 204 as will be discussed in more detail below, rather than a difference in fabrication.

The relative positioning of the tube 202 and the grasping fibers 204 may determine whether the manipulator 120 is in an open state or a closed state. A hand-held controller, such as the hand-held controller 130 of FIG. 1, may be provided to control the relative positioning as desired. As the distal end 206 of the tube 202 comes closer to the distal ends of the grasping fibers 204, the manipulator 120 enters a closed state. As the distal ends of the grasping fibers 204 and the tube 202 move apart, the manipulator assumes an open state due to the opposite curve directions of the up group 204A and the down group 204B.

Figure 2D:
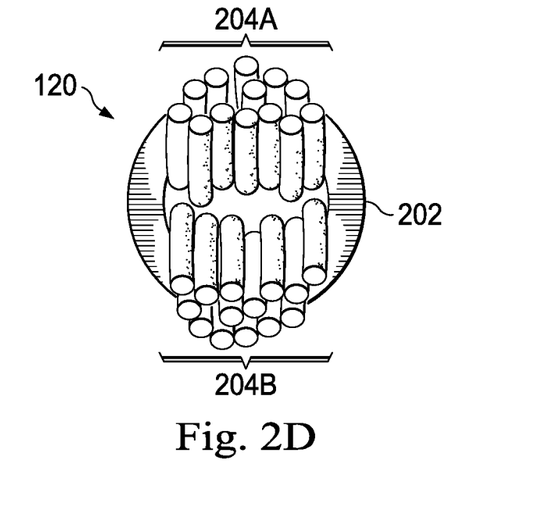
FIG. 2D is an end view of the retinal manipulator as illustrated in FIG. 2C.

FIG. 2D is an end view of the retinal manipulator illustrated in FIGS. 2A, 2B, and 2C. As depicted, in FIG. 2D, the manipulator 120 is in an open state. When the manipulator 120 is in an open state, it may be used to grasp delicate tissue as illustrated in FIGS. 3A and 3B.

Figure 3A:
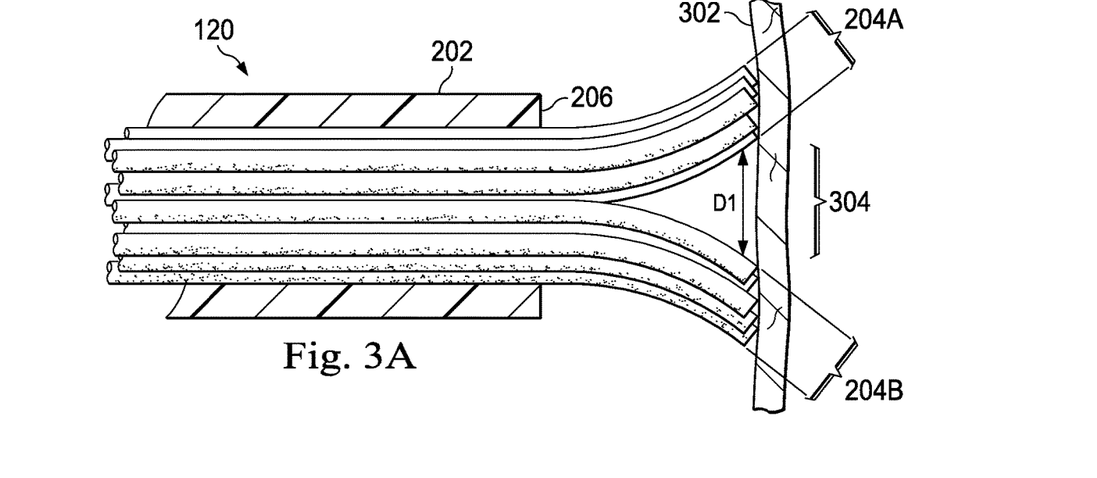
FIG. 3A is a cross-sectional illustration of an open-state retinal manipulator in contact with retinal tissue according to exemplary aspects of the present disclosure.

FIG. 3A is a cross-sectional illustration of the retinal manipulator 120 of FIGS. 2A-D in contact with retinal tissue 302 according to exemplary aspects of the present disclosure. During a procedure requiring retinal manipulation, the distal end of the manipulator 120 is carefully maneuvered into contact with the tissue 302, which has detached from the sclera as described above in FIG. 1. As illustrated in FIG. 3A, the manipulator 120 is in an open state, such that the up group 204A and the down group 204B of the grasping fibers 204 are separated by a separation distance D1 of about 0.2 millimeters to about 1 millimeter.

Figure 3B:
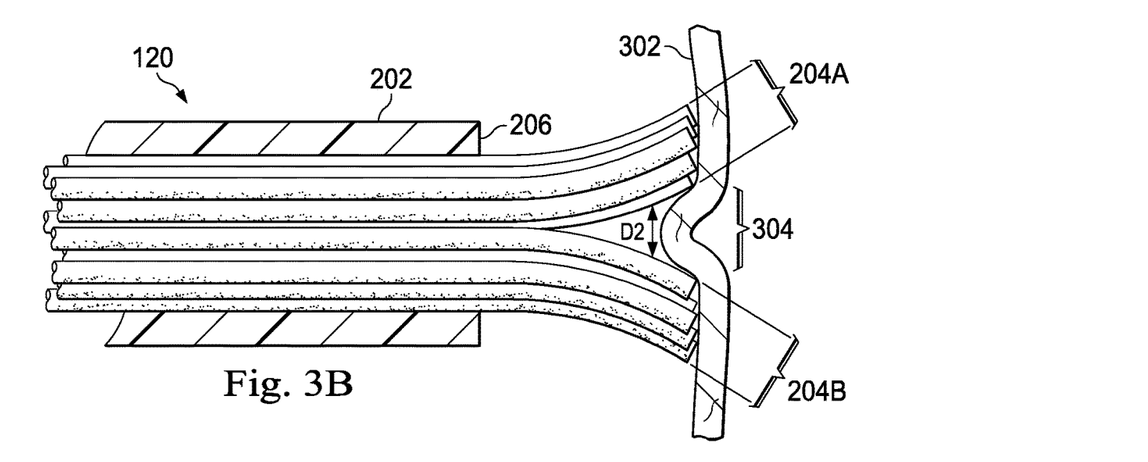
FIG. 3B is a cross-sectional illustration of a grasping-state retinal manipulator in contact with retinal tissue according to exemplary aspects of the present disclosure.

FIG. 3B illustrates the retinal manipulator 120 in a grasping state. When the manipulator 120 is desirably positioned in contact with the tissue 302, the tube 202 of the manipulator 120 is moved forward (i.e., distally) relative to the grasping fibers 204. As the tube 202 moves toward the distal ends of the grasping fibers 204, the tube 202 forces the up group 204A and the down group 204B closer together. In some embodiments, the grasping fibers may be moved proximally toward a proximal end of the tube 202. As the grasping fibers 204 are forced together by the tube 202, the separation distance decreases as indicated by a smaller separation distance D2 in FIG. 3B. A section 304 of the tissue 302 is pinched or grasped between the up group 204A and the down group 204B, such that manipulation of the tissue 302 may be accomplished by maneuvering the manipulator 120.

Figure 3C:
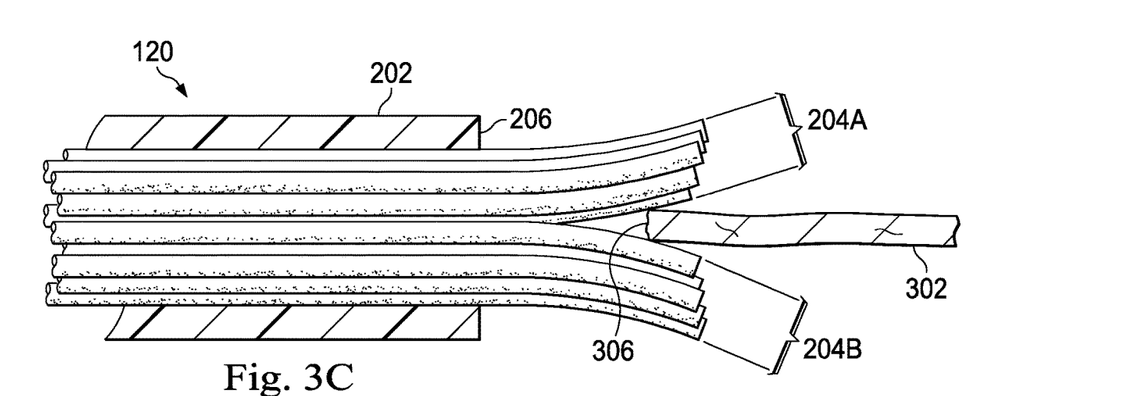
FIG. 3C is a cross-sectional illustration of a grasping-state retinal manipulator in contact with a loose end of retinal tissue according to exemplary aspects of the present disclosure.

FIG. 3C also illustrates the retinal manipulator 120 in a grasping state. FIG. 3C is similar to FIG. 3B in many respects, but illustrates a different way in which the manipulator 120 may be used to manipulate the tissue 302. Rather than grasping a section 304 of the tissue 302, the manipulator 120 may be used to grasp and manipulate a loose end 306 of the tissue 302. The loose end 306 may be caused by a torn retina. The flexible grasping fibers 204 of the manipulator 120 may allow a surgeon to grasp the loose end 306 without damaging the tissue 302.

The grasping state may be achieved when the tube 202 is at a closest point to the distal ends of the grasping fibers 204, or may be achieved in a position between a fully closed state and a fully open state. The grasping fibers 204 may be flexible so that, even when the manipulator is in a fully closed position a separation distance D2 is present. This may prevent the section 304 of tissue 302 from being damaged by the manipulator 120 when in a grasping state. As illustrated, the grasping fibers 204 are formed from a polymer material, such as polyurethane, nylons, and polypropylene. In other embodiments the grasping fibers 204 are formed from other polymers, glass, silicone, metal, a composite, or another suitable material. Each individual fiber of the grasping fibers 204 may have an outer diameter ranging from about 0.01 millimeters to about 0.1 millimeters. In general, the higher the elastic modulus of the material used, the smaller cross-section of the fibers may be. As illustrated in FIG. 3B, the grasping fibers 204 distribute the force exerted by the manipulator 120. As depicted, not all of the fibers 204 are in contact with the tissue 302. However, the fibers 204 may fan out horizontally in response to each other and to the exerted force as the grasping state is achieved, further increasing the contact area.

The stiffness of the grasping fibers may be predictably altered by varying the distance the grasping fibers extend beyond the distal end of the tube 202. For example, when the grasping fibers are fully extended as illustrated in FIG. 3A, the fibers may be at their most flexible, least stiff configuration. In such an open or extended state, the manipulator 120 may be suitable for delicate tasks such as smoothing or flattening wrinkles from the retinal tissue 302 with minimal adverse impact. Thus, a surgeon may use the manipulator 120 both to grasp the tissue 302 for larger scale repositioning of a detached portion of the tissue 302 and for finer scale smoothing of the tissue 302 once it has been placed back into contact with the back of the eye.

Figure 4A:
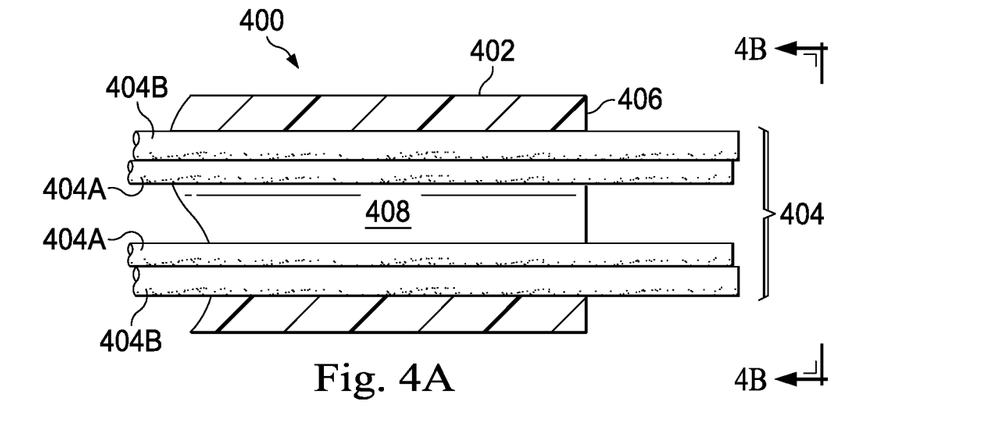
FIG. 4A is a cross-sectional illustration of an alternative retinal manipulator in a closed state according to exemplary aspects of the present disclosure.
Figure 4B:
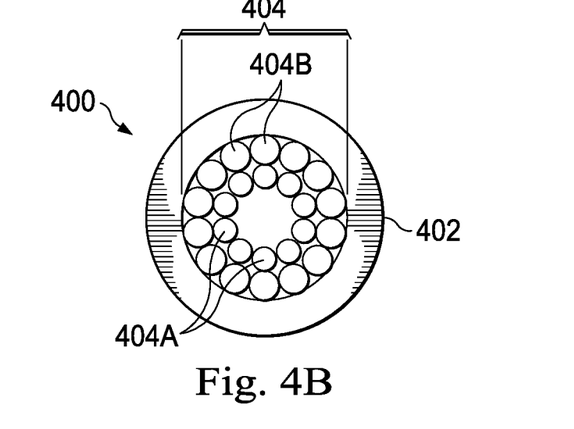
FIG. 4B is an end view of the alternative retinal manipulator illustrated in FIG. 4A.

FIGS. 4A, 4B, 4C, and 4D illustrate an additional embodiment of a manipulator that may be used as the retinal manipulator 120 of FIG. 1. FIG. 4A is a cross-sectional view of a distal portion of a delicate tissue manipulator 400. The manipulator 400 is similar in many respects to the manipulator 120 described above, and includes an elongate member or tube 402 and a plurality of grasping fingers 404. The tube 402 includes a distal end 406 and a proximal end (not depicted). In the illustrated embodiment, the tube 402 is a metal tube that has an outer diameter ranging from about 0.4 millimeters to about 0.9 millimeters. The grasping fibers 404 are configured in two concentric rings of fibers: a ring of inner fibers 404A and a ring of outer fibers 404B. Both the inner fibers 404A and the outer fibers 404B extend through a lumen 408 running through the tube 402. FIG. 4A illustrates the manipulator 400 in a closed state such that it may not be used for grasping tissue. In some embodiments, when the manipulator 400 is in a closed state, the grasping fibers 404 may be fully retracted within the tube 402. The grasping fibers 404 may be fully retracted when inserted into the eye. FIG. 4B also illustrates the manipulator 400 in a closed state, but from an end view perspective.

Figure 4C:
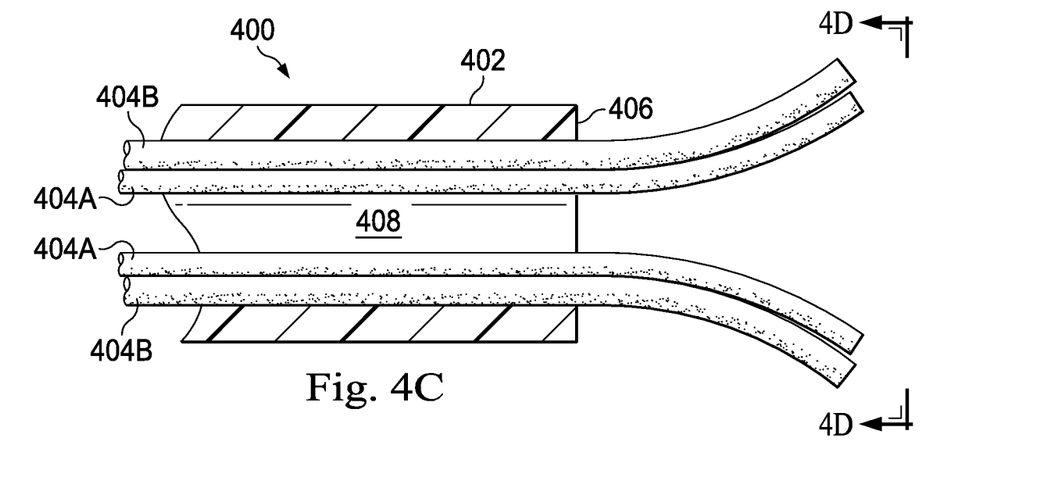
FIG. 4C is a cross-sectional illustration of the alternative retinal manipulator of FIGS. 4A and 4B in an open state according to exemplary aspects of the present disclosure.
Figure 4D:
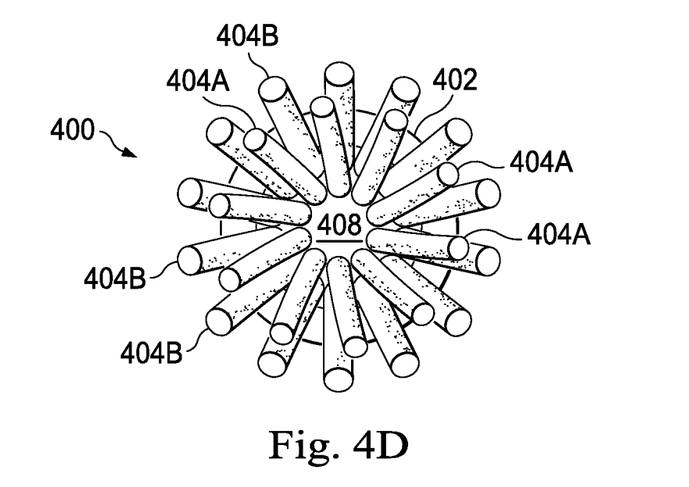
FIG. 4D is an end view of the retinal manipulator as illustrated in 4C.

FIGS. 4C and 4D illustrate the manipulator 400 in an open state such that it can be used to grasp delicate tissue. The grasping fingers 404, both in inner fibers 404A and the outer fibers 404B, are configured such that as the distal end 406 of the tube 402 moves away from distal ends of the fibers 404, each fiber moves away from a central axis of the tube 402. This may be better understood with reference to FIG. 4D. As illustrated in the end view of FIG. 4D, in the open state, the inner fibers 404A and the outer fibers 404B form circles expanding away from a central axis of the tube 402. The manipulator 404 may be able to circumferentially grasp a portion of delicate tissue by which to manipulate the tissue. The manipulator 120 may provide a comparatively more bilateral grasp on the tissue.

Figure 5A:
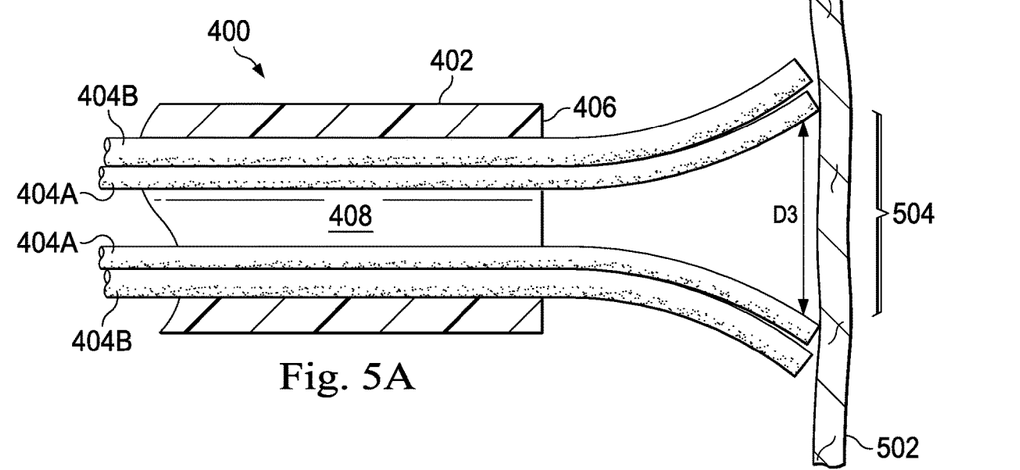
FIG. 5A is a cross-sectional illustration of the alternative retinal manipulator of FIGS. 4A-D in contact with retinal tissue according to exemplary aspects of the present disclosure.
Figure 5B:
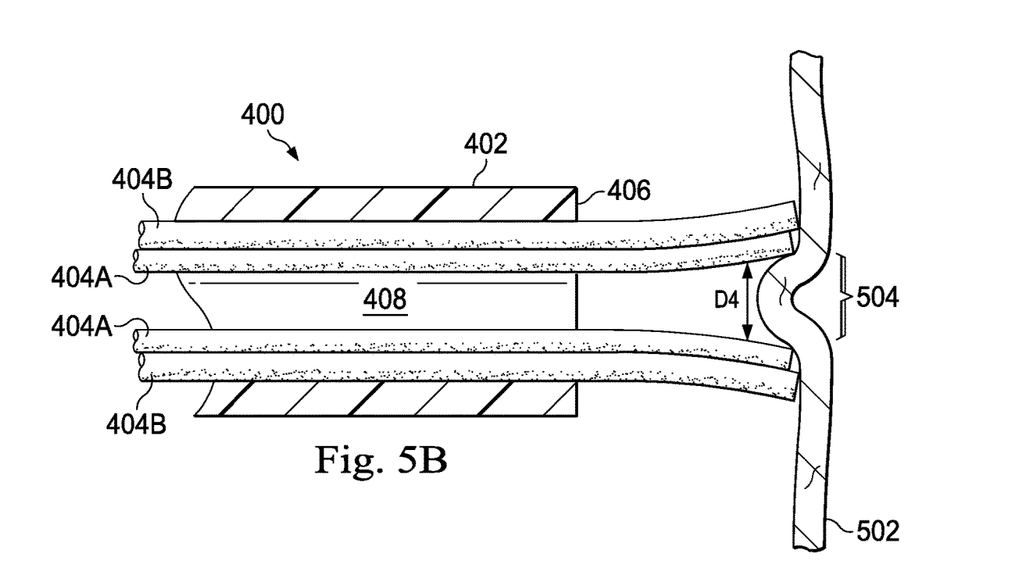
FIG. 5B is a cross-sectional illustration of the retinal manipulator of FIG. 5A in a grasping state according to exemplary aspects of the present disclosure.

FIGS. 5A and 5B illustrate the manipulator 400 in use. In FIG. 5A, the manipulator is carefully positioned proximate a tissue 502, such as retinal tissue, in an open state, such that a separation distance D3 is opened and available to grasp a section 504 of the tissue 502. As the distal end 406 of the tube 402 is moved closer to the distal ends of the fibers 404, the tube 402 forces the fibers 404 closer together, decreasing the separation distance D3, and grasping the section 504 as illustrated in FIG. 5B. In the grasping state, the manipulator 400 includes a separation distance D4 between the distal ends of the grasping fibers 404. As described above, the manipulator 400 grasps circumferentially, such that the view of FIG. 5B may be substantially the same from any perspective orthogonal to a central axis of the tube 402. As described open in connection with the manipulator 120 in FIGS. 3A and 3B, the manipulator 400 may be used to reposition the tissue 502 in the open (or extended) state and in the grasping state.

Figure 6:
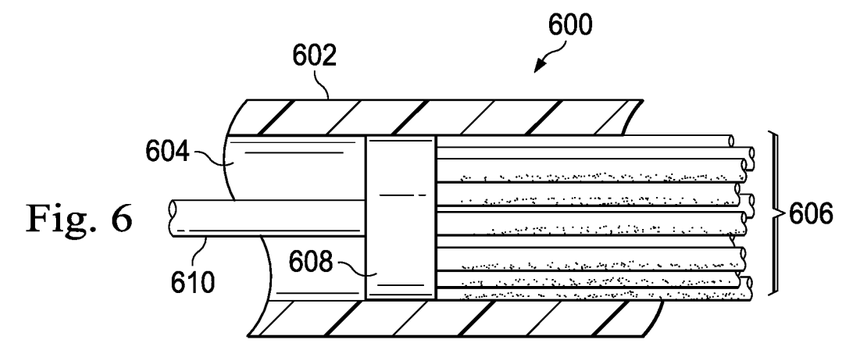
FIG. 6 is a cross-sectional illustration of a portion of a retinal manipulator according to exemplary aspects of the present disclosure.

FIG. 6 is a cross-sectional illustration of a portion of a manipulator 600. The manipulator 600 is similar to the manipulator 120 and the manipulator 400 described above. However, the distal portion of the manipulator 600 is not illustrated in FIG. 6, rather a more central portion of the manipulator 600 is presented. The manipulator 600 includes a tube 602, which is similar to the tubes 202 and 402 and has a lumen 604 extending therethrough. Proximal ends of a plurality grasping fibers 606 are coupled to a slide block 608 so that the grasping fibers 606 may be moved together as a single group. In turn, the slide block 608 is coupled to an attachment line 610 that connects with a controller, such as the hand-held controller 130 of FIG. 1.

The controller may be a squeeze-type controller that can allow a surgeon or technician using the manipulator 600 (or the manipulators 120 and/or 400) to squeeze the controller to transition from an open state to a closed state or to a grasping state having tissue secured by the grasping fibers 606 of the manipulator 600. As such, in some embodiments, the controller 130 also serves as the handle to the manipulator. Alternatively, the controller may be a slide-type controller that permits a surgeon to control the state of the controller by manipulating a sliding mechanism. As such, the controller may act as a piston or plunger that advances the slide block 608, causing the grasping fibers to project relative to the distal end of the tube. In some embodiments, the attachment line 610 fixes the grasping fibers in place while the controller is configured to move the tube 602 relative to the grasping fibers. Other controls, both manual, and automated, are contemplated. Some embodiments include biasing members, such as spring-actuators, that bias the manipulator 600 to a position placing the manipulator in an open state.

The slide block 608 may be formed from plastic, metal, a composite, or other material, and may be insertably or abuttingly coupled with the grasping fibers 606. All of the grasping fibers 606 may be formed so that they curve when not constrained by the tube 602. By selectively arranging and coupling the grasping fibers 606 to the slide block, a desired open state may be achieved. For example, if a first group of fibers is inserted so that they bend up when not constrained and a second group of fibers is inserted so that they bend down when not constrained, the manipulator 600 may have an open state similar to that depicted in FIGS. 2C and 2D. Alternatively, the grasping fibers may be inserted into the slide block 608 so that the manipulator 600 has an open state similar to that depicted in FIGS. 4C and 4D. To maintain orientation within the tube 602, the slide block 608 may be cylindrically shaped with an outer diameter that approximates an inner diameter of the tube 602.

The attachment line 610 may rigidly couple the slide block 608 to the controller so that the slide block 608 may be selectively moved forward and backward along a portion of the lumen 604. Additionally, using a manipulator as described herein may entail using the controller to move the tube 602 relative to the slide block 608 affixed to a rigid attachment line 610. While the attachment line 610 is depicted as having a smaller outer diameter than that of the slide block 608, in some embodiments the outer diameter of the attachment line 610 may substantially conform to an inner diameter of the tube 602.

Figure 7:
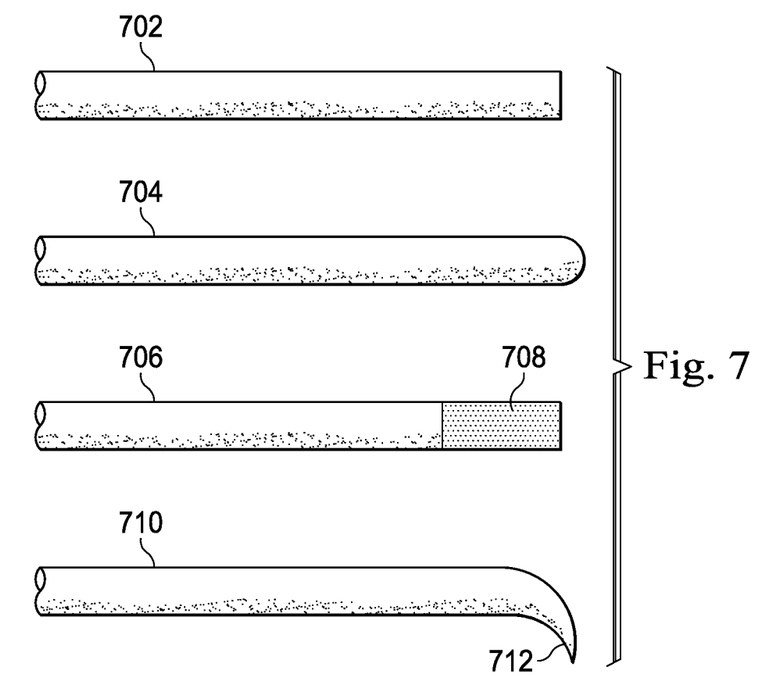
FIG. 7 is a side-view illustration of a plurality of exemplary distal ends of a grasping fiber according to exemplary aspects of the present disclosure.

FIG. 7 is a side-view illustration of a plurality of exemplary distal ends of individual grasping fibers. The distal ends depicted in FIG. 7 may be present on the grasping fibers described above in connection with manipulators 120, 400, and 600. An exemplary grasping fiber 702 includes a distal end that is straight. An exemplary grasping fiber 704 has a rounded distal end. An exemplary grasping fiber 706 includes a textured area 708 at its distal end. The textured area 708 may provide more adhesion when grasping delicate tissues. FIG. 7 also includes an exemplary grasping fiber 710 that includes a hook 712 at its distal end. While the grasping fibers of a manipulator may be formed from a variety of materials, fibers like the grasping fiber 710 may be more easily formed from plastic than glass or metal. Combinations of the features of grasping fibers 702, 704, 706, and 710 may be used as well to decrease the pressure needed to securely manipulate delicate tissues. In some embodiments of a manipulator as described herein may include more than one type of grasping fiber.

Figure 8:
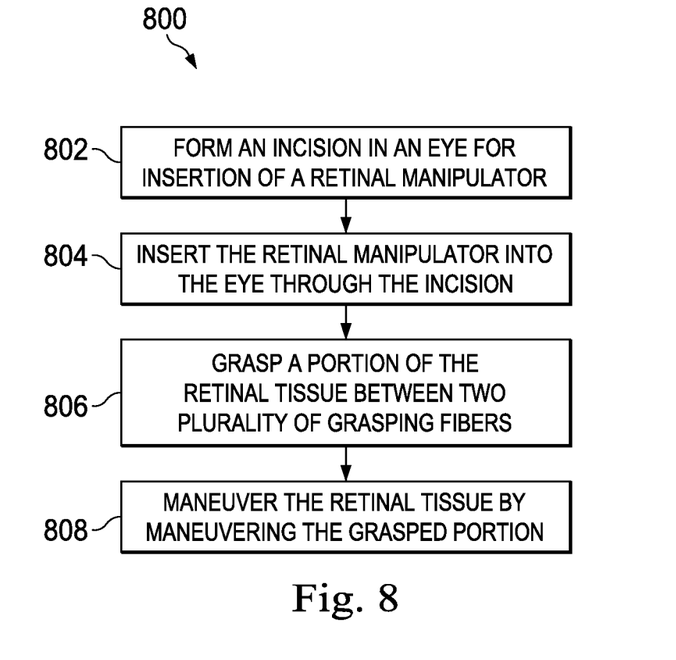
FIG. 8 is a flowchart of a method of positioning retinal tissue that has detached from a back surface of an eye according to exemplary aspects of the present disclosure.

FIG. 8 is a flowchart of a method 800 of positioning retinal tissue that has detached from a back surface of an eye of a patient. As illustrated in FIG. 8, the method 800 includes a plurality of enumerated steps. Embodiments of the method 800 may include additional steps before, after, and in between the enumerated steps. Method 800 begins in step 802 in which a surgeon makes an incision in the eye, such as the eye 100 of FIG. 1 and performs any needed surgical processes, such as a vitrectomy process. In step 804, the surgeon inserts a retinal manipulator into the eye of the patient through the incision. The retinal manipulator inserted in step 804 may be similar in shape and function to the manipulator 120 of FIGS. 1, 2A-D, and 3A-B or the manipulator 400 of FIGS. 4A-D and 5A-B. Before inserting the manipulator into the eye, the surgeon may fully retract the plurality of grasping fibers into the tube of the manipulator as described above.

In step 806, the surgeon grasps a portion of the detached retinal tissue using the plurality of grasping fibers as included in the manipulator 120 or the manipulator 400. In step 808, the surgeon maneuvers the retinal tissue into a desired position by maneuvering a proximal end of the retinal manipulator. This may largely alter the general position of the retinal tissue. The surgeon may additionally use the plurality of grasping fibers in an extended or open state, thereby making the grasping fibers less stiff, to smooth wrinkles from the retinal tissue or otherwise provide finer scale positioning.

The systems and methods disclosed herein may be used to reposition delicate tissues, such as retinal tissue, within a patient. This may result in more desirable positioning and also may result in less damage to the tissue resulting from the repositioning process. A single apparatus may be used for larger scale movements and finer scale movements of the tissue. This may improve the efficiency and efficacy of procedures performed with these systems and methods.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of positioning retinal tissue that has detached from a back surface of an eye of a patient, the method comprising:
    making an incision in the eye;
    inserting a retinal manipulator into the eye through the incision, the retinal manipulator having two pluralities of grasping fibers at a distal end thereof;
    grasping a portion of the retinal tissue that is detached from the back surface of the eye between the two pluralities of grasping fibers; and
    maneuvering the retinal tissue by maneuvering the grasped portion with the retinal manipulator.

2. The method of claim 1, wherein the retinal manipulator comprises a tube having the two pluralities of grasping fibers positioned therein, the two pluralities of grasping fibers being biased to extend in different directions.

3. The method of claim 2, further comprising adjusting a stiffness of the plurality of grasping fibers by positioning the tube relative to the two pluralities of grasping fibers.

4. The method of claim 1, further comprising fully retracting the two pluralities of grasping fibers into a tube prior to inserting the retinal manipulator into the eye through the incision.

* * * * *